United States Patent [19]

Sheedy

[11] Patent Number: 5,661,539
[45] Date of Patent: Aug. 26, 1997

[54] VISUAL TOOL FOR ASSESSING THE ERGONOMIC POSITION OF A VIDEO DISPLAY TERMINAL

[76] Inventor: James E. Sheedy, 136 Hillcroft Way, Walnut Creek, Calif. 94596

[21] Appl. No.: 325,993

[22] Filed: Oct. 18, 1994

[51] Int. Cl.⁶ ................................................. A61B 3/02
[52] U.S. Cl. ........................................ 351/239; 351/222
[58] Field of Search ................................ 351/239, 211, 351/237, 246, 222, 223, 244, 245; 128/630; 606/204.25; 359/436

[56] References Cited

U.S. PATENT DOCUMENTS

| 4,365,873 | 12/1982 | Ginsburg | 351/239 |
| 4,611,893 | 9/1986 | Schrier | 351/239 |

OTHER PUBLICATIONS

Brochure "Ergo Measure Tool," Herman Miller, Inc., 1992.
Brochure "Vision Tester," Bausch & Lomb Scientific Optical Products Division, 1985 (estimate).
Brochure "VDU Eye Screening Test," 1992 (estimate).
"6 No–Nonsense Ways to Help Computer Users," Optometric Management, Jun. 1992.

*Primary Examiner*—Hung X. Dang
*Attorney, Agent, or Firm*—Workman, Nydegger & Seeley

[57] ABSTRACT

A novel apparatus for assessing and quantifying the ergonomic position of a video display terminal (VDT) is disclosed. In the preferred embodiment, the apparatus includes a substantially planar measurement tool having a plurality of measurement indicia formed on the front side thereof. The measurement indicia are arranged so as to indicate the distance in inches above and below an alignment indicator formed at the center of the measurement tool. The tool also includes an adhesive portion so that it can be affixed to the VDT in a manner such that the alignment indicator is substantially aligned with the center of the VDT screen. In another embodiment, the measurement tool includes two visual acuity charts, which allow for the testing of the VDT operator's visual acuity. In another embodiment, the measurement tool includes an elongate measurement tape, affixed to the front side of the tool, for determining the viewing distance between the operator and the VDT.

21 Claims, 2 Drawing Sheets

VISUAL TOOL FOR ASSESSING THE ERGONOMIC POSITION OF A VIDEO DISPLAY TERMINAL

BACKGROUND OF THE INVENTION

1. Technical Field

The present invention relates generally to health-related symptoms and problems resulting from the use of video display terminals and related computer equipment. More particularly, the present invention is directed to a unique apparatus and method for assessing and quantifying the correct ergonomic position of a video display terminal.

2. Background Information

In the past 15 years, the number of individuals using computers has increased at a phenomenal rate. This growth can be attributed primarily to the development and widespread availability of personal or desk-top type computers equipped with video display terminals (VDTs). In fact, it is estimated that within the near future a majority of office workers will be using computers on a regular basis.

Although this increased use of computers is highly beneficial, it has also resulted in a variety of unfortunate side-effects. Often, these side-effects are related to various computer-induced disorders that result from the visual demands of regular and prolonged use of a computer equipped with a VDT. Symptoms often complained of include: headaches, near blurred vision, slowness in focusing (distance to near and back), double vision, eyestrain, glare sensitivity, eye irritation, and neck, back and shoulder pain.

Frequently, these and other symptoms are attributable to an improper arrangement of a computer operator's work environment. A computer operator's entire body posture is dictated by what he or she is viewing and, with a fixed element such as a VDT, the operator will typically position the body so that the eyes can see comfortably. If the operator must assume an uncomfortable position to properly see the VDT, many of the above problems can occur—especially in individuals who spend long periods of time working at a computer.

Consequently, the proper positioning and orientation of the computer and the video display terminal is extremely important to an operator's visual and physical health. Optimally, the VDT must be positioned so that it is comfortable both for the eyes and for the body. For instance, studies have shown that for most operators a VDT should be positioned ten (10) to twenty (20) degrees below the operator's line of sight. A VDT that is positioned improperly (high or low) can: cause eye irritation (often caused by a below-normal blink rate); stress the operator's accommodative system (i.e., a reduced amplitude of accommodation); and place physical stress on the operator's neck, back and/or shoulders.

In addition, an improper viewing distance between the operator and the VDT can also result in various computer-induced disorders. Although there can be a wide range of acceptable viewing distances depending on the particular type of screen being used and the type of tasks being performed, a viewing distance between twenty (20) to twenty-eight (28) inches is most common. If the distance is outside of this range, there could be undue stress on the operator's eyes and/or body position. Also, an improper viewing distance could indicate underlying visual problems, or could be contributing to other symptoms.

Whether a VDT is properly positioned is also highly dependent on the particular operator's visual acuity (i.e., ability to see detail). If an operator's visual acuity is inadequate when viewing the VDT, various visual symptoms can occur. Also, poor acuity can also cause the operator to make unnatural posture adjustments that can result in the various physiological problems associated with computer usage. Further, many computer operators have prescription lenses, such as bifocals or other multifocal lenses. Although these lenses are satisfactory for the majority of daily visual requirements, they may be entirely inappropriate for the viewing distances and viewing angles associated with computer and VDT usage.

The various computer-induced symptoms that result from an improper positioning of the computer VDT are of utmost concern. Such symptoms can greatly reduce a computer operator's productivity, and can potentially lead to more chronic health problems. Obviously, both computer operators and their employers have a need to identify and correct such problems, and more importantly, to prevent their occurrence in the first instance.

Fortunately, the underlying causes can often be corrected or prevented by merely rearranging the operator's work environment and/or by using appropriate occupational prescription lenses. Up until now however, operators are often unaware that such problems can be caused by improperly positioned computer equipment. Similarly, operators have not had the tools necessary to simply and effectively assess, and solve any problems in their work environments. Even optometrists and other health care providers often have a difficult time diagnosing computer-induced vision disorders. Even when the problem is correctly identified, these professionals typically lack the diagnostic information needed to make the appropriate recommendations.

OBJECTS AND BRIEF SUMMARY OF THE INVENTION

The present invention has been developed in response to the present state of the art, and in particular, in response to these and other problems and needs that have not been fully or completely solved by currently available solutions for rectifying the underlying causes of the various computer-induced vision disorders and physiological problems. It is therefore a primary object of the present invention to provide a novel apparatus and method for assessing and quantifying the optimum ergonomic position of a computer's video display terminal.

Another object of the present invention is to provide an apparatus and method that can be used by the individual operator to evaluate whether his or her VDT is positioned correctly.

Yet another object of the present invention is to provide an apparatus and method that allows an operator to determine whether the height of a VDT is optimal.

A related object of the present invention is to provide an apparatus and method that allows an operator to assess the viewing distance between the operator and the VDT screen.

Still another object of the present invention is to provide an apparatus and method that allows an operator to assess whether his or her own visual acuity is adequate for working with the VDT.

Another object of the present invention is to provide an apparatus and method that allows an operator to obtain objective data about his or her own work environment that can then be related to a health care provider, thereby allowing for a more complete and accurate diagnosis and prescription. These and other objects and features of the present invention will become more fully apparent from the following description and appended claims, or may be learned by the practice of the invention as set forth hereinafter.

Briefly summarized, the foregoing and other objects are achieved with a novel apparatus and method for assessing and quantifying the ergonomic position of an operator's video display terminal. Advantageously, the apparatus and method is simple to use, and can be used directly by the computer operator. The apparatus and method provides the operator with the data needed to make any necessary changes to the work environment, and can alert the operator to a need for further treatment by an eye doctor or other health care professional.

In a preferred embodiment, the apparatus of the present invention comprises a substantially planar measurement tool having a plurality of measurement indicia (preferably showing inches, or some other suitable measurement gradient) formed on the front side of the tool. The measurement indicia indicate the vertical distance above and below an alignment indicator placed on the front side of the tool. The tool can be positioned on the display screen side of a VDT, preferably by way of a suitable attachment means, in a manner such that the alignment indicator is substantially aligned with the center of the VDT screen. When so positioned, the operator can assess relative the height of the VDT screen based on the operator's horizontal line of sight. If needed, the VDT screen can then be raised or lowered according to predetermined optimum heights.

In another embodiment, the tool includes a measurement means, affixed to the front side of the tool, for measuring the viewing distance between the video display and the operator of the video display. The measurement tool also preferably includes visual acuity means, also placed on the front side of the tool, for assessing the visual acuity of the VDT operator.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not to be considered to be limiting of its scope, the invention in its presently understood best mode will be described and explained with additional specificity and detail through the use of the accompanying drawings in which.

DETAILED DESCRIPTION OF THE PREFERRED EMBODIMENTS

Figure 1:
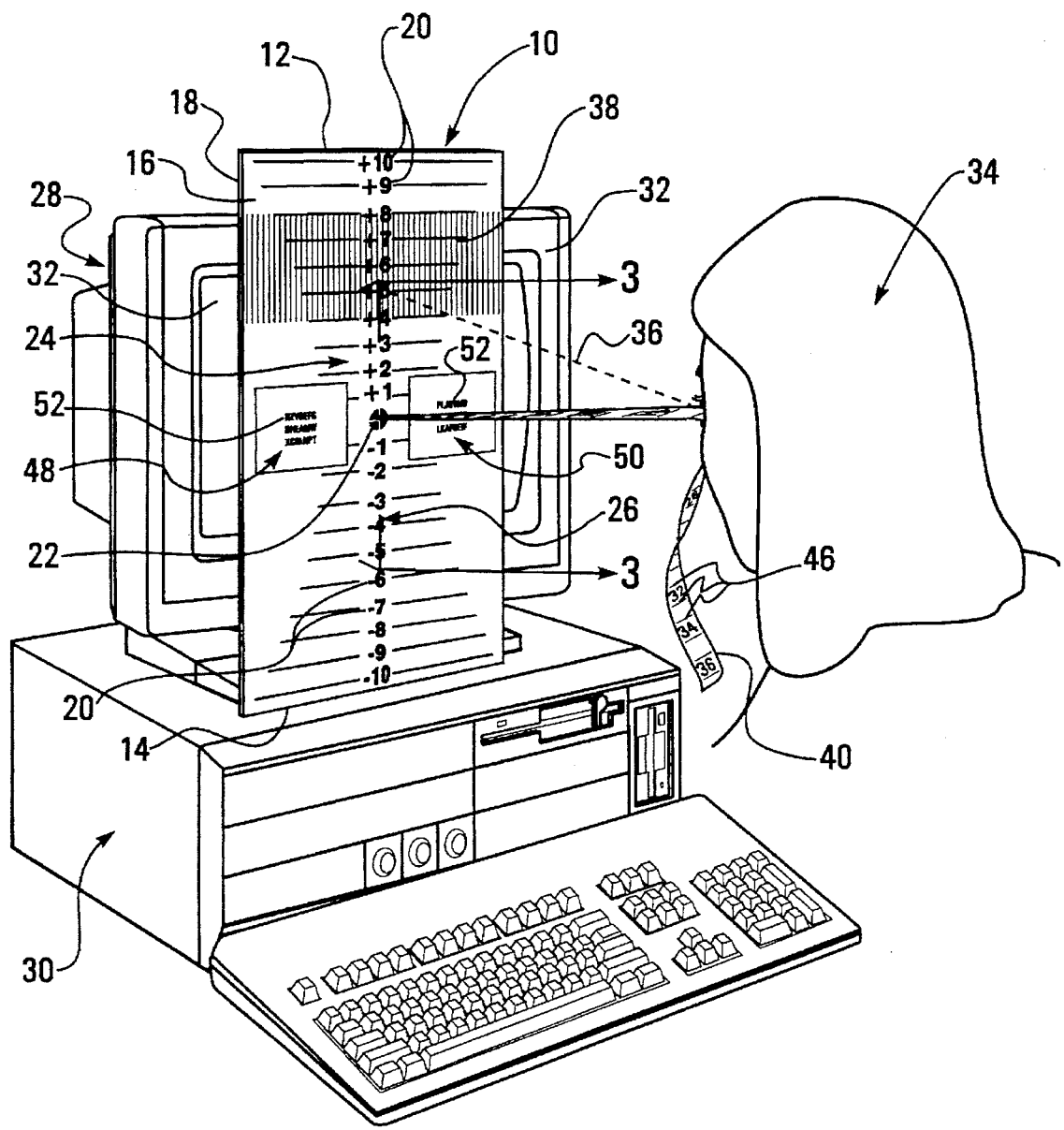
FIG. 1 is perspective view of the apparatus of the present invention affixed to a video display terminal portion of a computer.

Referring first to FIG. 1, the apparatus of the present invention is illustrated as comprising a measurement tool, generally designated at 10. Preferably, measurement tool 10 is substantially planar, and includes a top 12 and a bottom 14 end and front 16 and back 18 sides. Measurement tool 10 is preferably formed from a stiff cardboard material, but can also be constructed from any similarly rigid, or semi-rigid material, such as plastic.

Figure 2:
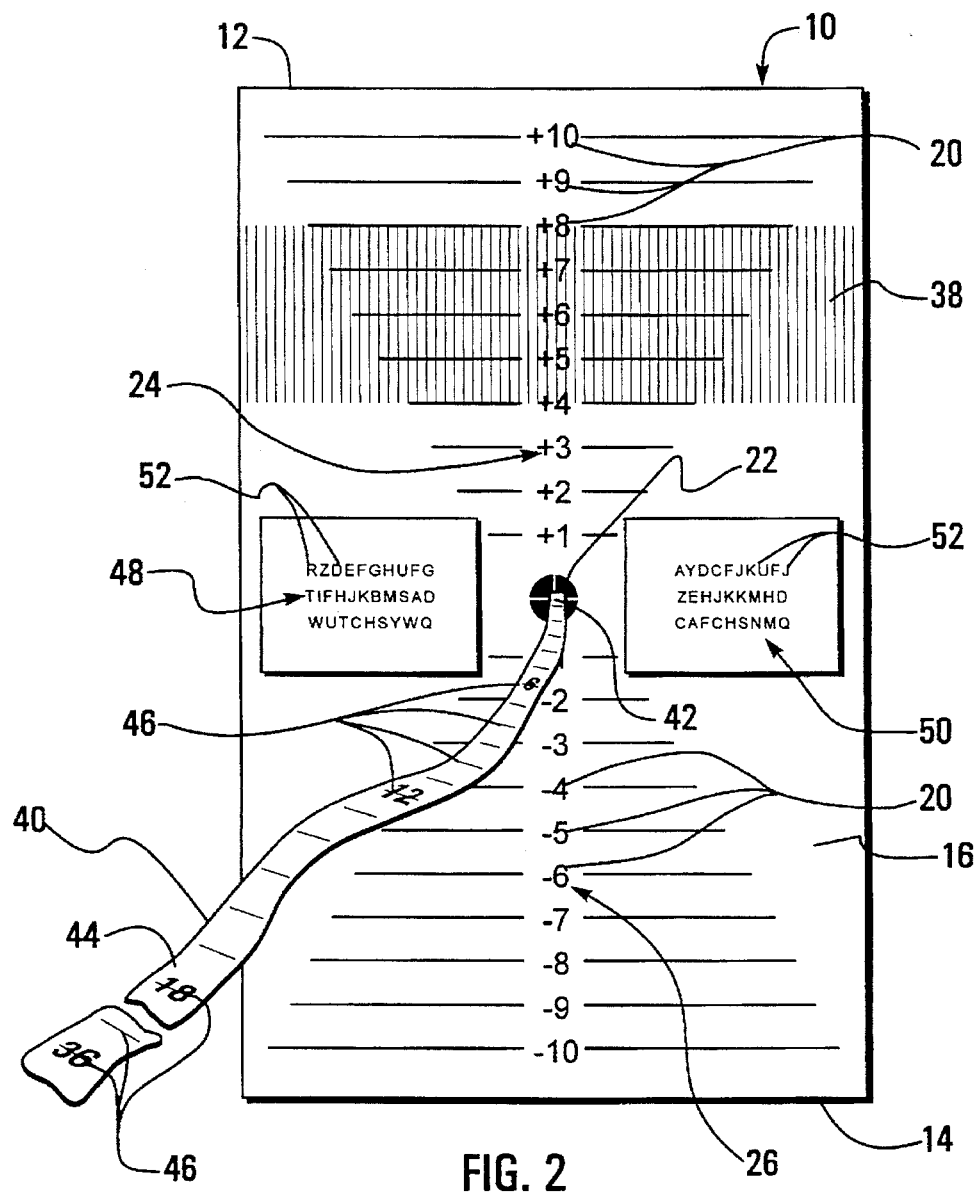
FIG. 2 is a front elevational view of the apparatus shown in FIG. 1.

As is shown in both FIGS. 1 and 2, formed on the front side 16 of tool 10 is a plurality of visually perceivable measurement indicia 20. In the preferred embodiment, the measurement indica 20 are each spaced apart in one-inch gradients with corresponding numerical indicators, although other distance gradients could also be used. As is shown, the indicia 20 are arranged on the front side 16 of the tool 10 so as to be oriented vertically between the top and bottom ends 12, 14. Also formed on the front side 16 of the tool 10 is an alignment indicator 22, which in the illustrated embodiment is placed at the center of tool 10.

With continued reference to FIGS. 1 and 2 together, the measurement indica 20 are preferably arranged into two sets. The first set, designated generally at 24, are positioned above the alignment indicator 22 and are arranged so as to denote a vertical distance, preferably in inches, above the indicator 22. Similarly, the second set, designated generally at 26, are positioned below the alignment indicator 22 so as to denote a vertical distance below the indicator 22. In the preferred embodiment, the measurement indicia 20 denote a distance of ten inches above, and ten inches below the alignment indicator, although other distances could be used.

FIG. 1 illustrates one method of using the measurement tool 10 so as to assess the height of a video display terminal (VDT), shown generally at 28, of the type commonly used in conjunction with a personal computer 30 or similar equipment. Measurement tool 10 is positioned, preferably by way of attachment means discussed below in connection with FIG. 3, on the from side 32 of VDT 28 so that the alignment indicator 22 is substantially aligned with the center of the VDT screen 32. When so positioned, the top and bottom ends 12, 14 of the tool extend above and below the VDT screen 32, as is shown. As such, it will be appreciated that the length of the measurement tool 10 may vary, depending on the size of the VDT screen 32 being used.

The operator 34 then views the measurement tool 10 in a manner such that the eye level is substantially horizontal, as is shown by the dotted line 36. The operator 34 can then determine which of the measurement indicia 20 substantially corresponds to the horizontal eye level 36. The particular measurement indicia 20 indicates the relative height of the center of the VDT screen 32. Thus, if the horizontal eye level 36 corresponds to the +8 inch indicia mark, then the center of the screen 32 is eight inches below the operator's eye level. Conversely, if it corresponds to the −5 inch indicia mark, then the center of the screen 32 is five inches above the operator's eye level 36.

Studies have shown that the VDT screen 32 should optimally be four to eight inches below the operator's eyes. The preferred embodiment includes a shaded region 38 on the front side 16 of the tool 10 located between the +4 inch indicia and the +8 inch indicia. If the operator's horizontal eye level 36 falls within this shaded region, then no adjustment of the VDT screen 32 is necessary. However, if it falls outside of this region then the screen height is not within an optimal range, and the operator can adjust the relative height of the VDT screen accordingly. It will be appreciated that what is considered an optimal height may vary depending on the type of VDT used, the type of work being done, and even on personal characteristics of the operator 34. As such, the shaded region 38 may be adjusted in different embodiments.

With continued reference to FIGS. 1 and 2 together, another preferred embodiment of the present invention includes a measurement means for measuring the viewing distance between the video display terminal and the operator. By way of example and not limitation, the measurement means is shown as comprising an elongate tape 40. The tape 40 is affixed (by way of staple, adhesive, or other suitable means) at one of its ends 42 to the front side 16 of the measurement tool 10, preferably at the position of the alignment indicator 22. Formed along the top side 44 of the tape 40 and along most of its length are a plurality of distance measurement indicia 46. These measurement indicia 46 are also preferably spaced apart and numerically represented in one-inch gradients, up to a length of thirty-six inches.

In use, the tape 40 is used to evaluate the viewing distance between the VDT screen 32 and the operator 34. To do so, the operator assumes a normal working position, and then extends the tape 40 to the bridge of the operator's nose. Under most conditions the optimum viewing distance should be approximately twenty to twenty-eight inches. The operator can use the measurement to adjust the viewing distance accordingly.

The tape 40 can also be used in connection with another preferred embodiment of the invention. In this embodiment, the measurement tool 10 further includes a visual acuity means for assessing the visual acuity of the operator of the display. By way of example and not limitation, the visual acuity means is illustrated in FIGS. 1 and 2 as comprising a left 48 and a right 50 visual acuity chart. The visual acuity charts 48, 50 are preferably positioned on respective sides of the alignment indicator 22, although other locations would be suitable.

Each of the visual acuity charts 48, 50 include a plurality of characters, such as the letters 52 shown, which are arranged into at least two rows. These letters 52 are preferably sized and spaced apart so as to test for a 20/25 acuity at a distance of twenty-four inches. It will be appreciated that, instead of letters 52, any similar series of characters or numerals could also be used. Also, tests for different levels of visual acuity can also be implemented. For instance, the size of the letters or characters can be changed and/or the testing can be conducted at viewing distances other than twenty-four inches.

In one preferred method, the operator will be positioned, by way of measurement taken with the tape 40, twenty-four inches from the VDT screen 32. The operator will then test each eye by covering one eye, and then determining whether each of the letters in the corresponding visual acuity chart 48, 50 can be seen with the open eye (i.e., left eye for the left acuity chart 48, and right eye for the right acuity chart 50). An inability to make out each of the letters 52 within the charts 48, 50 indicates a possible visual acuity problem. In such a case, the operator should probably be examined by an eye doctor so that the problem can be corrected, possibly with prescription lenses specifically designed for work at a VDT.

Figure 3:
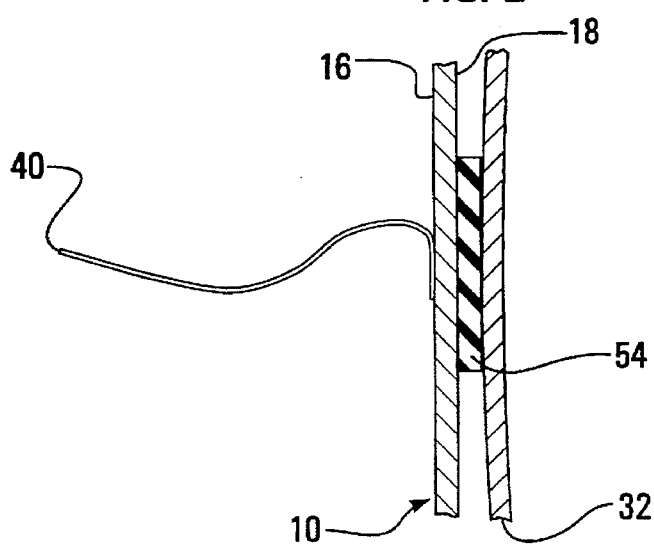
FIG. 3 is a cross-sectional view, taken along lines 3—3 in FIG. 1, showing an adhesive portion used to releasably affix the measurement tool to the VDT.

FIG. 3 illustrates how in the preferred embodiment the measurement tool 10 includes attachment means for releasably affixing the tool 10 to the video display 28. By way of example and not limitation, the attachment means comprises at least one adhesive portion 54, such as would be found on peel-away self-sticking adhesive materials. This adhesive portion 54 can be formed on the back side 18 of the measurement tool 10 so that the tool 10 can be temporarily affixed to the front 32 of the VDT 28 such that the alignment indicator 22 is substantially aligned with the center of the VDT screen 32. In the preferred embodiment, a single adhesive portion 54 is oriented so that the tool 10 is affixed directly to the screen 32. Other points of attachment could also be used.

The adhesive portion 54 is of a type so that the tool 10 can be easily removed from the VDT 10 when the tool's use is complete. It will be appreciated that other means of affixing the tool 10 to the VDT 28 are equivalent to the adhesive portion 54 illustrated, and thus fall within the intended scope of the invention. For example tape, clips, Velcro, other adhesives, or other similar attachment means could also be used.

In summary, the present invention is directed to an apparatus that allows a computer operator to identify and then correct any problems associated with the positioning of the operator's video display terminal. Farther, the apparatus allows the operator to identify whether he or she has visual problems that should be addressed by an eye doctor. In this way, the operator and the doctor can together diagnose, and then correct, the underlying causes of many computer-induced vision and physical symptoms. Further, the apparatus can be used to set up an operator's computer environment so that computer-induced disorders are prevented in the first instance.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. An apparatus for assessing and quantifying the ergonomic position of a video display terminal, the apparatus comprising:

a substantially planar measurement tool having a top and a bottom end and a front and a back side, the tool further including a plurality of visually perceivable measurement indicia placed on the front side of the tool, each of the measurement indicia being spaced apart and separated by a fixed predetermined distance and arranged so as to be oriented vertically between said top end and said bottom end and wherein the plurality of measurement indicia are arranged so as to indicate a vertical distance from an alignment indicator positioned on the front side of the measurement tool; and attachment means for releasably affixing said measurement tool to the video display terminal in a manner such that said alignment indicator is substantially aligned with a center point location on said video display terminal.

2. An apparatus as defined in claim 1, wherein the plurality of measurement indicia are arranged in a first set and a second set, the first set being arranged so as to indicate a first distance above said alignment indicator positioned on the front side of the measurement tool, and the second set being arranged so as to indicate a second distance below the alignment indicator, whereby said first distance corresponds to the distance above the center point location on the video display terminal and said second distance corresponds to the distance below the center point location on the video display terminal.

3. An apparatus as defined in claim 2, further comprising visual acuity means, placed on the front side of said measurement tool, for assessing the visual acuity of an operator of the video display terminal.

4. An apparatus as defined in claim 3, wherein the visual acuity means comprises a left-eye visual acuity chart and a right-eye visual acuity chart, the left-eye visual acuity chart and the right-eye visual acuity chart both comprising a plurality of letters having a predetermined size and the plurality of letters being arranged into at least two rows.

5. An apparatus as defined in claim 4, further comprising measurement means, affixed to the front side of the measurement tool, for measuring a distance between the video display terminal and an operator of the video display terminal.

6. An apparatus as defined in claim 5, wherein the measurement means comprises an elongate and flexible tape having one end affixed to the front side of the measurement tool, the tape further including a plurality of distance measurement indicia placed along the length of the tape.

7. An apparatus as defined in claim 6, wherein the attachment means comprises at least one adhesive portion formed on the measurement tool, the adhesive portion being capable of releasably adhering the measurement tool to the video display terminal.

8. An apparatus as defined in claim 2, further comprising measurement means, affixed to the front side of the measurement tool, for measuring a distance between the video display terminal and an operator of the video display terminal.

9. An apparatus as defined in claim 8, further comprising visual acuity means, placed on the front side of said measurement tool, for assessing the visual acuity of an operator of the video display terminal.

10. An apparatus for assessing and quantifying the ergonomic position of a video display terminal, the apparatus comprising:
- a substantially planar measurement tool having a top and a bottom end and a front and a back side, the measurement tool further including a plurality of visually perceivable measurement indicia placed on the front side of the tool, each of the measurement indicia being spaced apart and separated by a fixed predetermined distance and arranged so as to be oriented vertically between said top end and said bottom end, and wherein the plurality of measurement indicia are arranged so as to indicate a vertical distance from an alignment indicator positioned on the front side of the tool;
- attachment means for releasably affixing said tool to the video display terminal in a manner such that said alignment indicator is substantially aligned with a center point location on said video display terminal;
- visual acuity means, placed on the front side of said tool, for assessing the visual acuity of the operator of the video display terminal; and
- measurement means, affixed to the front side of the tool, for measuring a distance between the video display terminal and an operator of the video display terminal.

11. A method for assessing and quantifying the ergonomic position of a video display terminal comprising the steps of:
- positioning a measurement tool having a plurality measurement indicia relative to the video display terminal in a manner such that an alignment indicator located on a front side of said measurement tool is substantially aligned with the center of said video display terminal;
- viewing said measurement tool in a manner such that the viewer's eye level is substantially horizontal with respect to the measurement tool;
- determining which of said measurement indicia substantially corresponds to said viewer's horizontal eye level; and
- determining whether the vertical position of the video display terminal is correct with respect to said viewer, depending on the location of the corresponding measurement indicia determined in the previous step.

12. A method as defined in claim 11, further comprising the step of determining the viewing distance between the viewer and the video display terminal.

13. A method as defined in claim 12, further comprising the step of determining the adequacy of the viewer's visual acuity based on whether the viewer can visually perceive, at a predetermined distance, a plurality of characters formed on a visual acuity chart positioned on the measurement tool.

14. An apparatus for assessing and quantifying the ergonomic position of a video display terminal, the apparatus comprising:
- measurement tool means for measuring the relative height of a video display terminal with respect to an operator of the video display terminal;
- measurement means, affixed to the measurement tool means, for measuring a viewing distance between the video display terminal and the operator of the video display terminal; and
- means for releasably affixing the measurement tool means to the video display terminal.

15. An apparatus for assessing and quantifying the ergonomic position of a video display terminal, the apparatus comprising:
- a measurement tool capable of being positioned substantially adjacent to the video display terminal, the tool including a plurality of visually perceivable measurement indicia placed on a front side of the tool, each of the measurement indicia being spaced apart and separated by a fixed predetermined distance and arranged so as to be oriented vertically on the front side, the plurality of measurement indicia being arranged so as to indicate a vertical distance from an alignment indicator positioned on the front side of the tool; and
- measurement means, affixed to the measurement tool, for measuring a viewing distance between the video display terminal and an operator of the video display terminal when the measurement tool is positioned substantially adjacent to the video display terminal.

16. An apparatus as defined in claim 15, wherein the plurality of measurement indicia are arranged in a first set and a second set, the first set being arranged so as to indicate a distance above said alignment indicator, and the second set being arranged so as to indicate the distance below the alignment indicator.

17. An apparatus as defined in claim 15, wherein the measurement means comprises an elongate tape having one end affixed to the front side of the measurement tool, the tape further including a plurality of distance measurement indicia placed along the length of the tape.

18. An apparatus as defined in claim 15, further comprising visual acuity means, placed on the front side of said measurement tool, for assessing the visual acuity of an operator of the video display terminal.

19. An apparatus as defined in claim 18, wherein the visual acuity means comprises at least one visual acuity chart, the at least one visual acuity chart comprising a plurality of symbols having a predetermined size and spaced apart relationship.

20. An apparatus as defined in claim 15, further comprising attachment means for releasably affixing said measurement tool to the video display terminal in a manner such that said alignment indicator is substantially aligned with a center point location on said video display terminal.

21. An apparatus as defined in claim 20, wherein the attachment means comprises at least one adhesive portion formed on the measurement tool, the adhesive portion being capable of releasably adhering the measurement tool to the video display terminal.

* * * * *